US009480437B2

(12) United States Patent
Watanabe et al.

(10) Patent No.: US 9,480,437 B2
(45) Date of Patent: Nov. 1, 2016

(54) MOVEMENT COMPENSATION FOR SUPERIMPOSED FLUOROSCOPY AND RADIOGRAPHY IMAGE

(71) Applicants: Koichiro Watanabe, Nasushiobara (JP);
Hisato Takemoto, Nasushiobara (JP);
Takayuki Ishikawa, Nasushiobara (JP);
Takuya Sakaguchi, Utsunomiya (JP)

(72) Inventors: Koichiro Watanabe, Nasushiobara (JP);
Hisato Takemoto, Nasushiobara (JP);
Takayuki Ishikawa, Nasushiobara (JP);
Takuya Sakaguchi, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 570 days.

(21) Appl. No.: 13/709,327

(22) Filed: Dec. 10, 2012

(65) Prior Publication Data
US 2013/0156154 A1   Jun. 20, 2013

(30) Foreign Application Priority Data

Dec. 20, 2011   (JP) ................. 2011-278836

(51) Int. Cl.
| | | |
|---|---|---|
| *A61B 6/06* | (2006.01) | |
| *A61B 6/02* | (2006.01) | |
| *A61B 6/00* | (2006.01) | |

(52) U.S. Cl.
CPC ............. *A61B 6/022* (2013.01); *A61B 6/06* (2013.01); *A61B 6/487* (2013.01); *A61B 6/5229* (2013.01); *A61B 6/4233* (2013.01); *A61B 6/4291* (2013.01); *A61B 6/4441* (2013.01)

(58) Field of Classification Search
CPC   A61B 8/5253; A61B 19/5244; A61B 6/463; A61B 6/5247; A61B 8/5261; A61B 1/0005; A61B 6/5229; A61B 6/487; A61B 6/5235; G21K 1/04; G21K 1/02; G21K 1/046; G01N 2223/1016; G01N 2223/316
USPC ..................................... 378/98.12
See application file for complete search history.

(56) References Cited

U.S. PATENT DOCUMENTS

| | | | | |
|---|---|---|---|---|
| 6,285,738 B1 * | 9/2001 | Nagai | ................ | A61B 6/4225 348/E5.087 |
| 6,493,575 B1 * | 12/2002 | Kesten | .................. | A61B 19/52 600/431 |

(Continued)

FOREIGN PATENT DOCUMENTS

| | | |
|---|---|---|
| JP | 2007-159913 A | 6/2007 |
| JP | 2008-132033 | 6/2008 |

(Continued)

OTHER PUBLICATIONS

Office Action issued Jun. 9, 2015 in Japanese Patent Application No. 2011-278836.

*Primary Examiner* — Brooke Purinton
(74) *Attorney, Agent, or Firm* — Oblon, McClelland, Maier & Neustadt, L.L.P.

(57) ABSTRACT

An X-ray diagnosis apparatus includes a radiography image generating unit, a fluoroscopy image generating unit, a display control unit and an irradiation field changing unit. The radiography image generating unit controls an X-ray irradiation device, an X-ray detection device, a retainer, and a bed system, and generates a radiography image by using a radiography irradiation field. The fluoroscopy image generating unit controls the X-ray irradiation device, the X-ray detection device, the retainer, and the bed system, and generates a fluoroscopy image by using a fluoroscopy irradiation field, the fluoroscopy irradiation field being narrower than the radiography irradiation field. The display control unit generates a superimposed image in which the fluoroscopy image is superimposed on a part of the radiography image, and displays the superimposed image on a display device. The irradiation field changing unit changes the fluoroscopy irradiation field with the superimposed image being displayed.

16 Claims, 10 Drawing Sheets

(56) References Cited

U.S. PATENT DOCUMENTS

| | | | |
|---|---|---|---|
| 7,634,308 B2* | 12/2009 | Ogawa | 378/98.12 |
| 8,880,153 B2* | 11/2014 | Pfister | 378/95 |
| 2003/0073901 A1* | 4/2003 | Simon | A61B 6/463 600/424 |
| 2005/0251028 A1* | 11/2005 | Boese et al. | 600/425 |
| 2005/0288578 A1* | 12/2005 | Durlak | 600/434 |
| 2009/0180591 A1* | 7/2009 | Baumgart | 378/98.12 |

FOREIGN PATENT DOCUMENTS

| | | |
|---|---|---|
| JP | 2011-507581 A | 3/2011 |
| JP | 2012-75782 | 4/2012 |

* cited by examiner

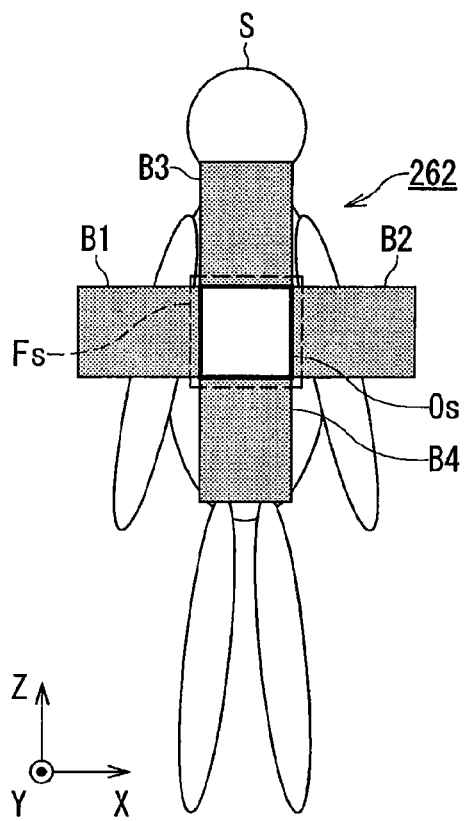 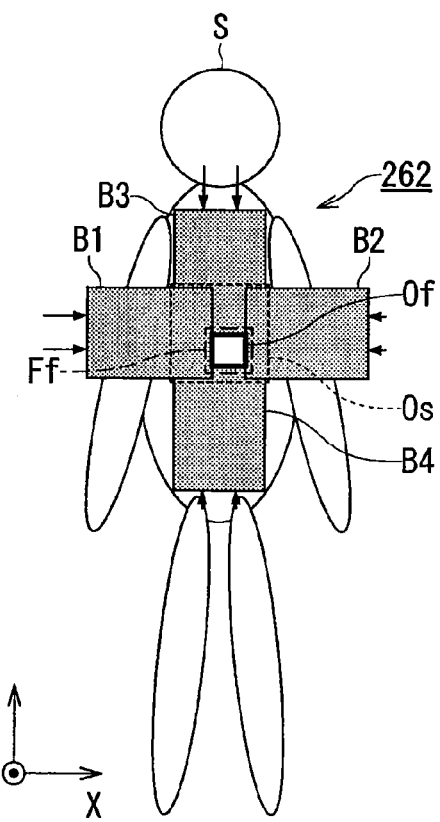
FIG. 3A  FIG. 3B
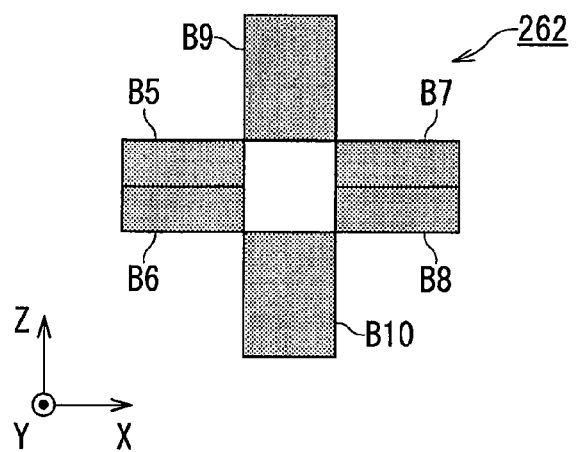
FIG. 4

MOVEMENT COMPENSATION FOR SUPERIMPOSED FLUOROSCOPY AND RADIOGRAPHY IMAGE

CROSS-REFERENCE TO RELATED APPLICATION

This application is based upon claims the benefit of priority from Japanese Patent Application No. 2011-278836, filed on Dec. 20, 2011, the entire contents of which are incorporated herein by reference.

FIELD

The present embodiment, as one aspect of the present invention, relates to an X-ray diagnosis apparatus and a control method thereof that performs fluoroscopy and radiography.

BACKGROUND

Conventionally, industry fields including nondestructive inspection and a medical field including medical check-ups, X-ray diagnosis apparatuses have been widely in use in which a target region or an object is irradiated with radiation (representatively, an X-ray) to detect intensity distribution of radiation having transmitted through the target region or object, yielding an image of the target region or object.

Further, in recent years, ablation procedures have been developed as methods of radical cure in therapies for arrhythmia. In the ablation procedure, confirming electrical conduction and confirming risk reduction are indispensable, and fluoroscopy/radiography continues for a long-time. As a result, the amounts of exposure on an operator and a patient become large. In view of this, techniques of partial fluoroscopy (Spot fluoroscopy) have been developed as a measure to reduce exposure during the fluoroscopy. It is extremely effective to utilize the partial fluoroscopy during the practice of the ablation procedure.

The partial fluoroscopy is a technique of performing fluoroscopy within a limited X-ray irradiation field by limiting the X-ray irradiation field during the fluoroscopy. The technique of the partial fluoroscopy narrows down an X-ray irradiation field for partial fluoroscopy, which is a field required for performing the fluoroscopy in an LIH (last image hold) image as a static image, and displays an image in such a manner as to superimpose, on a part of the LIH image, the fluoroscopy image as a dynamic image based on the fluoroscopy. The partial fluoroscopy is of use for, in particular, intervention of lower limbs, heart, and head part. The partial fluoroscopy can realize exposure reduction by approximately 80% by being used in combination with other low radiation dose techniques.

FIG. 12 is a diagram for explaining a first example of the partial fluoroscopy of conventional techniques.

FIG. 12 shows four X-ray irradiation fields F31-F34, and four images I31-I34 respectively corresponding thereto. Each of the X-ray irradiation fields F31-F34 includes a portion of interest P of the object. Images I31, I32, and I34 are superimposed images displayed during the partial fluoroscopy, in which a partial fluoroscopy image R is superimposed on a part of an LIH image L. The LIH image L in the superimposed image I31 is an image upon setting an X-ray irradiation field Ff for partial fluoroscopy; in other words, an image before change of relative positions of the object and an X-ray detection device.

Before the change of the relative positions of the object and the X-ray detection device, the content within an X-ray irradiation field Fs for radiography in the X-ray irradiation field F31, and the content of the LIH image L in the superimposed image I31 approximately agree with one another. Further, before the change of the relative positions of the object and the X-ray detection device, the content within the X-ray irradiation field Ff for partial fluoroscopy in the X-ray irradiation field F31 and the content of the partial fluoroscopy image R in the superimposed image I31 approximately agree with one another.

Here, there is a case where the relative positions of the object and the X-ray detection device are changed with the superimposed image I31 being displayed during the partial fluoroscopy. For example, in a case where the X-ray detection device is slid in a horizontal direction during the partial fluoroscopy, the X-ray irradiation field Fs for radiography and the X-ray irradiation field Ff for partial fluoroscopy are changed from as shown in X-ray irradiation field F31 to as shown in the X-ray irradiation field F32. Then, the superimposed image I32 is displayed. Here, in the superimposed image I32, the partial fluoroscopy image R in which the relative positions of the object and the X-ray detection device have been changed is superimposed on the LIH image L before the change of the relative positions of the object and the X-ray detection device.

According to the conventional technique shown in FIG. 12, in a case where the X-ray detection device is slid in the horizontal direction with the superimposed image I31 being displayed during the partial fluoroscopy, there is a case where, as shown in X-ray irradiation field F32, the portion of interest P comes out of the X-ray irradiation field Ff for partial fluoroscopy. In this case, the partial fluoroscopy is interrupted and the LIH radiography is again performed in the X-ray irradiation field Fs for radiography shown in the X-ray irradiation field F33, and an LIH image I33 is generated and displayed. When an operator such as operators of the fluoroscopy and radiography again sets the X-ray irradiation field Ff for partial fluoroscopy as shown in the X-ray irradiation field F34, the superimposed image I34 in which the partial fluoroscopy image R is superimposed on a part of the LIH image I33 is generated and displayed.

FIG. 13 is a diagram for explaining a second example of the partial fluoroscopy of the conventional techniques.

FIG. 13 shows two X-ray irradiation fields F31, F35 and two images I31, I35 respectively corresponding thereto. Each of the X-ray irradiation fields F31, F35 includes the portion of interest P of the object. The images I31, I35 are superimposed images in which the partial fluoroscopy image R is superimposed on a part (or whole) of the LIH image L displayed during partial fluoroscopy. The X-ray irradiation field F31 and the superimposed image I31 are equivalent to those shown in FIG. 12.

According to the conventional technique shown in FIG. 13, in a case where the X-ray detection device is slid in the horizontal direction with the superimposed image I31 being displayed during partial fluoroscopy, when the operator stops down an aperture, the X-ray irradiation field Fs for radiography and the X-ray irradiation field Ff for partial fluoroscopy are changed from as shown in the X-ray irradiation field F31 to as shown in the X-ray irradiation field F35. In other words, a movable aperture device has to be back to the normal fluoroscopy position (full-open position of the aperture blade). Then, the superimposed image I35 is displayed.

BRIEF DESCRIPTION OF THE DRAWINGS

In accompanying drawings,

FIGS. 3A and 3B are diagrams for explaining an aperture of an X-ray irradiation field;

FIG. 4 is a deformation example of FIGS. 3A and 3B;

DETAILED DESCRIPTION

Figure 1:
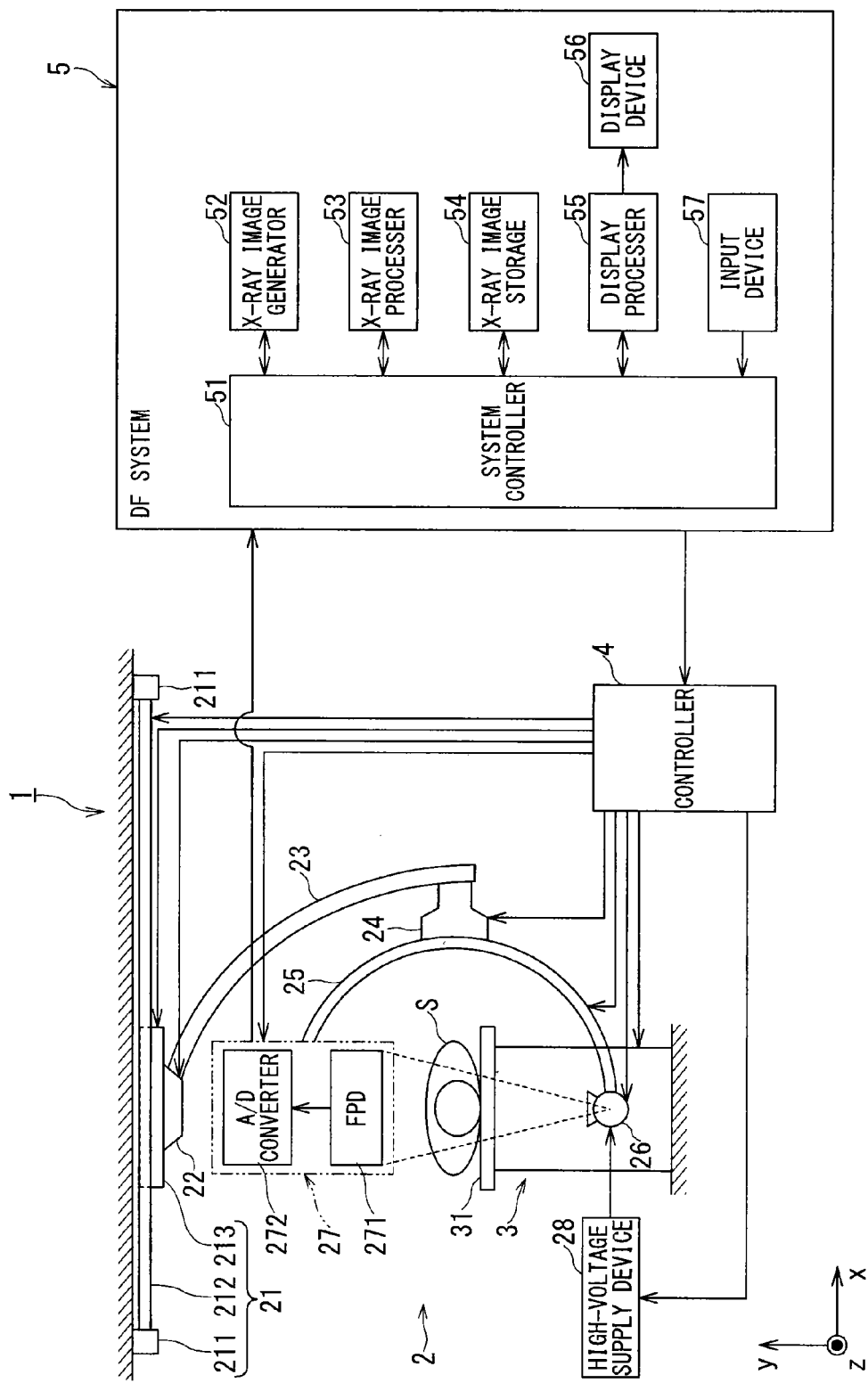
FIG. 1 is a schematic diagram showing a configuration of an X-ray diagnosis apparatus according to a present embodiment.

An X-ray diagnosis apparatus and a control method thereof of the present embodiment will be described with reference to the accompanying drawings.

To solve the above-described problems, the X-ray diagnosis apparatus according to the present embodiment includes: an X-ray irradiation device configured to irradiate an object with an X-ray, the device including an X-ray source configured to generate an X-ray and a movable aperture device configured to form an X-ray irradiation field; an X-ray detection device disposed to be opposed to the X-ray irradiation device and configured to detect the X-ray; a retainer configured to retain the X-ray irradiation device and the X-ray detection device; a bed system provided between the X-ray irradiation device and the X-ray detection device, and configured to place an object thereon; a radiography image generating unit configured to control the X-ray irradiation device, the X-ray detection device, the retainer, and the bed system, and to generate a radiography image as a static image by using a radiography irradiation field as the X-ray irradiation field; a fluoroscopy image generating unit configured to control the X-ray irradiation device, the X-ray detection device, the retainer, and the bed system, and to generate a fluoroscopy image as a dynamic image by using a fluoroscopy irradiation field as the X-ray irradiation field, the fluoroscopy irradiation field being narrower than the radiography irradiation field; a display control unit configured to generate a superimposed image in which the fluoroscopy image is superimposed on a part of the radiography image, and to display the superimposed image on a display device; and an irradiation field changing unit configured to change the fluoroscopy irradiation field with the superimposed image being displayed.

To solve the above-described problems, the X-ray diagnosis apparatus according to the present embodiment includes: an X-ray irradiation device configured to irradiate an object with an X-ray, the device including an X-ray source configured to generate an X-ray and a movable aperture device configured to form an X-ray irradiation field; an X-ray detection device disposed to be opposed to the X-ray irradiation device and configured to detect the X-ray; a retainer configured to retain the X-ray irradiation device and the X-ray detection device; a bed system provided between the X-ray irradiation device and the X-ray detection device, and configured to place an object thereon; a radiography image generation unit configured to control the X-ray irradiation device, the X-ray detection device, the retainer, and the bed system, and to generate a radiography image as a static image by using a radiography irradiation field as the X-ray irradiation field; a fluoroscopy image generation unit configured to control the X-ray irradiation device, the X-ray detection device, the retainer, and the bed system, and to generate a fluoroscopy image as a dynamic image by using a fluoroscopy irradiation field as the X-ray irradiation field, the fluoroscopy irradiation field being narrower than the radiography irradiation field; a display control unit configured to generate a superimposed image in which the fluoroscopy image is superimposed on a part of the radiography image, and to display the superimposed image on a display device; and an irradiation field changing unit configured to enlarge/contract the fluoroscopy irradiation field with a fluoroscopy irradiation field center as a center, while the superimposed image is displayed.

To solve the above-described problems, a control method for the X-ray diagnosis apparatus according to the present embodiment includes: an X-ray irradiation device configured to irradiate an object with an X-ray, the device including an X-ray source configured to generate an X-ray and a movable aperture device configured to form an X-ray irradiation field; an X-ray detection device disposed to be opposed to the X-ray irradiation device and configured to detect the X-ray; a retainer configured to retain the X-ray irradiation device and the X-ray detection device; and a bed system provided between the X-ray irradiation device and the X-ray detection device, and configured to place an object thereon, comprising: controlling the X-ray irradiation device, the X-ray detection device, the retainer, and the bed system, and to generate a radiography image as a static image by using a radiography irradiation field as the X-ray irradiation field; controlling the X-ray irradiation device, the X-ray detection device, the retainer, and the bed system, and generating a fluoroscopy image as a dynamic image by using a fluoroscopy irradiation field as the X-ray irradiation field, the fluoroscopy irradiation field being narrower than the radiography irradiation field; generating a superimposed image in which the fluoroscopy image is superimposed on a part of the radiography image, and displaying the superimposed image on a display device; and changing the fluoroscopy irradiation field with the superimposed image being displayed.

Figure 2:
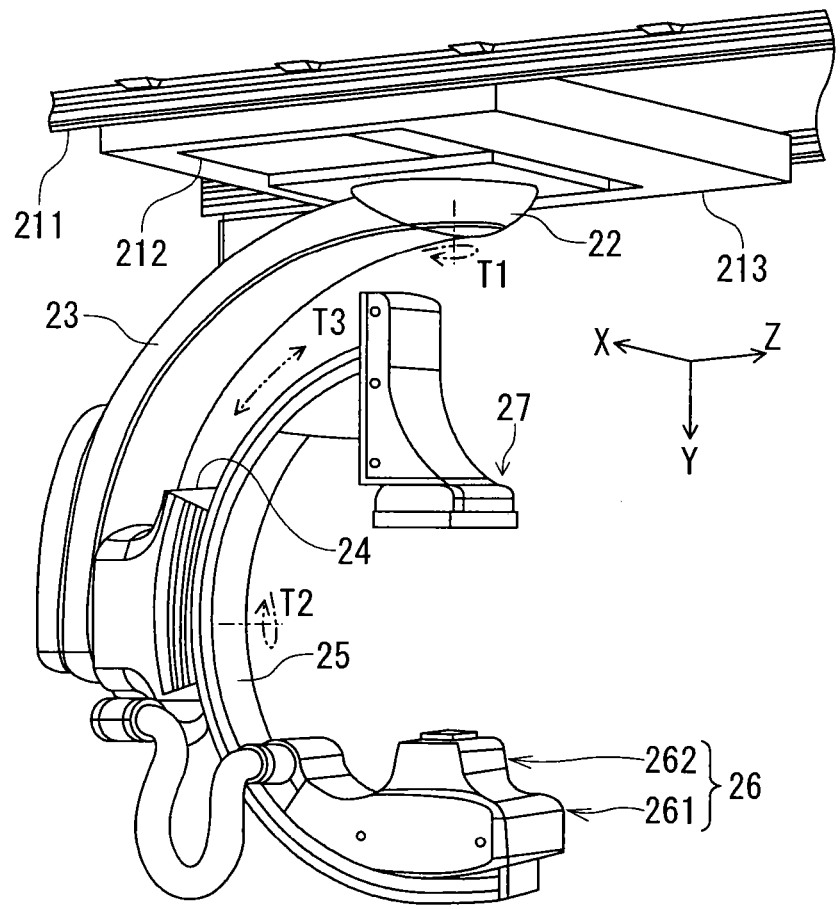
FIG. 2 is a perspective view showing an external appearance configuration of an imaging system in the X-ray diagnosis apparatus according to the present embodiment.

FIG. 1 is a schematic diagram showing a configuration of an X-ray diagnosis apparatus according to the present embodiment. FIG. 2 is a perspective view showing an external appearance configuration of an imaging system in the X-ray diagnosis apparatus according to the present embodiment.

FIG. 1 and FIG. 2 show an X-ray diagnosis apparatus 1 including a C-arm of a ceiling travel type of the present embodiment. The X-ray diagnosis apparatus 1 is roughly constituted of an imaging system 2, a bed system 3, a controller 4, a digital fluorography (DF) system 5. While the imaging system 2, the bed system 3 and the controller 4 are, in general, installed in a surgical operating room (or a room for check-up and/or medical treatment), the DF system 5 is installed in a control room adjoining to the surgical operating room. The X-ray diagnosis apparatus according to the present embodiment is not imitated to the X-ray diagnosis apparatus 1 including a C-arm of ceiling travel type, but may be an X-ray diagnosis apparatus including a C-arm of floor type or an Ω arm of ceiling travel type. Further, the X-ray diagnosis apparatus according to the present embodiment may be an X-ray diagnosis apparatus that does not include any C-arm.

The imaging system 2 is provided with a sliding mechanism 21, a vertical axis rotation mechanism 22, an overhang arm 23, a C-arm rotating mechanism 24, a C-arm 25, an X-ray irradiation device 26, an X-ray detection device 27, and a high-voltage supply device 28.

The sliding mechanism 21 is provided with a Z-axis direction rail 211, an X-axis direction rail 212, and a carriage 213. The sliding mechanism 21 slides the vertical axis rotation mechanism 22, the overhang arm 23, the C-arm rotating mechanism 24, the C-arm 25, the X-ray irradiation device 26, and the X-ray detection device 27 as one unit in a horizontal direction by control of the controller 4.

The Z-axis direction rail 211 extends in a Z-axis direction (long-axis direction of a table-top 31), and is supported by a ceiling.

The X-axis direction rail 212 extends in an X-axis direction (short-axis direction of the table-top 31), and is supported by the Z-axis direction rail 211 via rollers (not shown) on both ends thereof. The X-axis direction rail 212 is moved in the Z-axis direction on the Z-axis direction rail 211 by the control of controller 4.

The carriage 213 is supported by the X-axis direction rail 212 via a roller (not shown). The carriage 213 is moved in the X-axis direction on the X-axis direction rail 212 by the control of the controller 4.

The X-axis direction rail 212 supporting the carriage 213 is movable in the Z-axis direction on the Z-axis direction rail 211, and the carriage 213 is movable in the X-axis direction on the X-axis direction rail 212. Therefore, the carriage 213 is movable in the horizontal direction (X-axis direction and Z-axis direction) within the surgical operating room.

The vertical axis rotation mechanism 22 is rotatably supported by the carriage 213. The vertical axis rotation mechanism 22 rotates the overhang arm 23, the C-arm rotating mechanism 24, the C-arm 25, the X-ray irradiation device 26, and the X-ray detection device 27 as one unit in a vertical axis rotation direction T1 (as illustrated in FIG. 2) by the control of the controller 4.

The overhang arm 23 is supported by the vertical axis rotation mechanism 22.

The C-arm rotating mechanism 24 is rotatably supported by the overhang arm 23. The C-arm rotating mechanism 24 rotates the C-arm 25, the X-ray irradiation device 26, and the X-ray detection device 27 as one unit in a rotation direction T2 against the overhang arm 23 (illustrated in FIG. 2) by the control of the controller 4.

The C-arm 25 is supported by the C-arm rotating mechanism 24 and positions the X-ray irradiation device 26 and the X-ray detection device 27 to be opposed to one another with an object S being as the center. On a back face or a side face of the C-arm 25 is provided with a rail (not shown). The C-arm 25, via the rail interposed between the C-arm rotating mechanism 24 and the C-arm 25, moves the X-ray irradiation device 26 and the X-ray detection device 27 as one unit in an arc direction T3 of the C-arm 25 (as illustrated in FIG. 2) by the control of the controller 4.

The X-ray irradiation device 26 is provided at one end of the C-arm 25. The X-ray irradiation device 26 is provided to be movable fore and aft by the control of the controller 4. The X-ray irradiation device 26 is provided with an X-ray tube (X-ray source) 261 and a movable aperture device 262.

The X-ray tube 261 receives supply of a high-voltage power from the high-voltage supply device 28 and generates an X-ray according to conditions of the high-voltage power.

The movable aperture device 262 movably supports an aperture blade formed of a material that screens the X-ray at an X-irradiation opening of the X-ray tube 261. On a front face of the X-ray tube 261, a radiation quality adjustment filter (not shown) to adjust radiation quality of the X-ray generated by the X-ray tube 261 may be provided.

FIGS. 3A and 3B are diagrams for explaining an aperture of an X-ray irradiation field. FIGS. 3A and 3B are diagrams in which the movable aperture device 262 is seen from the side of the X-ray tube 261.

The movable aperture device 262 shown in FIGS. 3A and 3B has four aperture blades B1-B4. The aperture blades B1-B4 are formed of, for example lead. The movable aperture device 262 shown in FIG. 3A shows a positioning (full-open) of the aperture blades B1-B4 on radiography, and the movable aperture device 262 shown in FIG. 3B shows a positioning of the aperture blades B1-B4 on partial fluoroscopy.

In the movable aperture device 262 shown in FIG. 3A, an aperture opening on radiography (hereafter referred to as "radiography opening") Os is formed by the aperture blades B1-B4. Further, based on the radiography opening Os, an X-ray irradiation field on radiography (hereafter referred to "radiography irradiation field") Fs is formed. Then, from the state shown in FIG. 3A, the radiography opening Os is narrowed (contracted) by adjustment of the positions in the X-axis direction of the aperture blades B1 and B2, which are movable in the X-axis direction, and by adjustment of the positions in the Z-axis direction of the aperture blades B3 and B4, which are movable in the Z-axis direction. When the radiography opening Os is contracted, an aperture opening on partial fluoroscopy narrower than the radiography opening Os (hereafter referred to "partial fluoroscopy opening") Of is formed (shown in FIG. 3B). Further, based on the partial fluoroscopy opening Of, an X-ray irradiation field on partial fluoroscopy that is narrower than the radiography irradiation field Fs (hereafter referred to as "partial fluoroscopy irradiation field") Ff is formed. In other words, in accordance with change from the radiography opening Os to the partial fluoroscopy opening Of, the size of the X-ray irradiation field (FOV: field of view) is changed from the radiography irradiation field Fs to the partial fluoroscopy irradiation field Ff.

The movable aperture device 262, receiving the supply of a driving signal from the controller 4, individually adjusts the aperture blades B1-B4. In other words, the aperture blades B1-B4 are connected to respective discrete drive mechanisms (motors).

Although the movable aperture device 262 shown in FIGS. 3A and 3B has been described as having the four aperture blades B1-B4, the present invention is not limited to this. For example, as shown in FIG. 4, the movable aperture device 262 may have six aperture blades B5-B10.

Referring back to FIG. 1 and FIG. 2, the X-ray detection device 27 is provided at another end of the C-arm 25 and opposed to the X-ray irradiation device 26. The X-ray detection device 27 is provided so as to be movable fore and aft by the control of the controller 4. The X-ray detection device 27 includes a flat panel detector (FPD) 271 and an analog to digital (A/D) converter 272.

The FPD 271 has a plurality of detector elements arrayed two-dimensionally. Between the detector elements of the FPD 271, a scanning line and a signal line are provided to be orthogonal to one another. A grid (not shown) may be provided on a front face of the FPD 271. In the grid, in order to improve the contrast of an X-ray image by absorbing scattered radiation entering the FPD 271, a grid panel formed of lead or the like whose X-ray absorption is large, and materials such as aluminum or wood that easily transmit X-ray, are alternately disposed.

The A/D converter 272 converts projection data of analog signals (video signals) output in time series from the FPD 271 to digital signals, and outputs the signals to the DF system 5.

The X-ray detection device 27 may be an image intensifier (I.I.)-TV system. In the I.I.-TV system, an X-ray having transmitted through the object S and an X-ray directly entering therein are converted to visible light. Furthermore, the projection data with high sensitivity is formed by doubling luminance through a process of light-to-electron/electron-to-light conversion and the optical projection data is then transformed into electric signals by using a charge coupled device (CCD) image sensor.

The high-voltage supply device 28 can supply a high-voltage power to the X-ray tube 261 of the X-ray irradiation device 26 in accordance with the control of the controller 4.

The bed system 3 is supported by a floor face and supports the table-top (catheter table) 31. The bed system 3 moves the table-top 31 to slide (in the X, Z-axes directions), displace above and below (in a Y-axis direction) and roll by the control of the controller 4. On the table-top 31, the object S can be placed. The following describes a case where the imaging system 2 is an under tube type in which the X-ray irradiation device 26 is located under the table-top 31. However, the imaging system 2 may be an over tube type in which the X-ray irradiation device 26 is located above the table-top 31.

The controller 4 includes a central processing unit (CPU) and a memory that are not shown. The controller 4, in accordance with the control of the DF system 5, controls driving of the sliding mechanism 21, the vertical axis rotation mechanism 22, the C-arm rotating mechanism 24, the C-arm 25, the X-ray irradiation device 26, and the X-ray detection device 27 of the imaging system 2, and driving of the bed system 3, as well as controlling operation of the X-ray irradiation device 26, the X-ray detection device 27, and the high-voltage supply device 28 for partial fluoroscopy and radiography.

The DF system 5 is a system that has a computer-based configuration and performs control of operation of the X-ray diagnosis apparatus 1 as a whole, and image processing related to a partial fluoroscopy image or a radiography image, which are acquired by the imaging system 2. The DF system S has a system controller 51, an X-ray image generator 52, an X-ray image processor 53, an X-ray image storage 54, a display processor 55, a display device 56, and an input device 57.

The system controller 51 includes a CPU and a memory that are not shown. The system controller 51 controls the controller 4 and each of the units 52 to 55 and 57.

The X-ray image generator 52, by the control of the system controller 51, performs a logarithmic transformation process (LOG process) on projection data output from the A/D converter 272 of the imaging system 2 and an addition process as needed, and generates data of the partial fluoroscopy image and the radiography image (digital angiography (DA) image).

The X-ray image processor 53 performs image processing on the partial fluoroscopy image and the radiography image generated by the X-ray image generator 52 by the control of the system controller 51. The image processing includes enlargement/gradation/spatial filter processes on data, minimum value/maximum value trace processes of data accumulated in time series, and addition processes to eliminate noise, etc. The data after the image processing by the X-ray image processor 53 is output to the display device 56 via the display processor 55, and, at the same time, stored in a storage device of the X-ray image storage 54, etc.

The display processor 55 synthesizes the partial fluoroscopy image and the radiography image which have been processed by the X-ray image processor 53, and a superimposed image in which the partial fluoroscopy image is superimposed on a part of the radiography image together with character information and granules of various parameters, etc. and outputs them to the display device 56 as a video signal by the control of the system controller 51.

The display device 56 displays the partial fluoroscopy image, the radiography image and the superimposed image output from the display processor 55, together with the character information and the granules of the various parameters, etc.

The input device 57 is a keyboard, mouse and the like that can be operated by the operator, and an input signal according to the operation is sent to the system controller 51.

Figure 5:
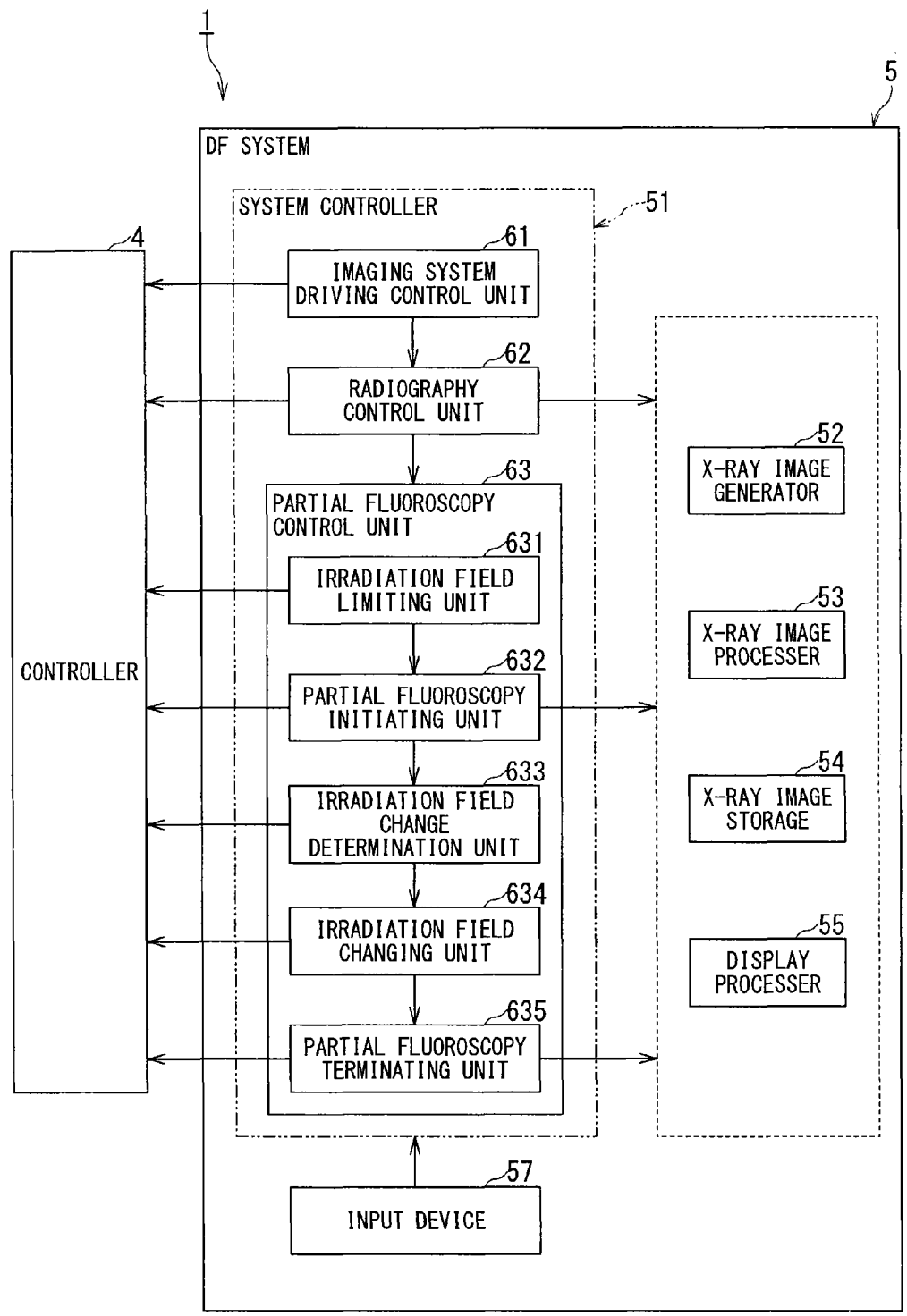
FIG. 5 is a block diagram showing a function of the X-ray diagnosis apparatus according to the present embodiment.

FIG. 5 is a block diagram showing a function of the X-ray diagnosis apparatus 1 according to the present embodiment.

The X-ray diagnosis apparatus 1 serves as an imaging system driving control unit 61, a radiography control unit 62, and a partial fluoroscopy control unit 63 as shown in FIG. 5, by the system controller 51 shown in FIG. 1 executing a program. Although each of the units 61 to 63 constituting the X-ray diagnosis apparatus 1 has been explained as operating by executing a program, the present invention is not limited to that case. The whole or a part of each of the units 61 to 63 constituting the X-ray diagnosis apparatus 1 may be included in the X-ray diagnosis apparatus 1 as hardware.

The imaging system driving control unit 61 has a function to control a position and an angle of X-irradiation by driving the imaging system 2 and the bed system 3 via the controller 4 in accordance with an instruction input from the input device 57, after the object S is placed on the table-top 31 of the imaging system 2. The imaging system driving control unit 61 adjusts the X-irradiation position by sliding at least one of the sliding mechanism 21 of the imaging system 2 and the table-top 31 of the bed system 3. The imaging system driving control unit 61 adjusts the X-irradiation angle by rotating at least one of the vertical axis rotation mechanism 22, the C-arm rotating mechanism 24, and the C-arm 25 of the imaging system 2, or by moving the C-arm 25 in the arc direction.

The radiography control unit 62 has a function to cause the X-ray detection device 27 and the high-voltage supply device 28 to operate and perform radiography via the controller 4, in accordance with the instruction input from the input device 57. Further, the radiography control unit 62 has a function to control the X-ray image generator 52, the X-ray image processor 53, the X-ray image storage 54, and the display processor 55 to generate and store an LIH image as a static image (the radiography image), or cause the display device 56 to display the LIH image.

The radiography control unit 62 performs the radiography only once before the partial fluoroscopy by the partial fluoroscopy control unit 63. Alternatively, the radiography control unit 62, in addition to the radiography before the partial fluoroscopy by the partial fluoroscopy control unit 63, temporarily interrupts the partial fluoroscopy after starting the partial fluoroscopy and performs the radiography during the interruption. In other words, with the superimposed image (for example, the superimposed image I1 shown in FIG. 8) being displayed, the LIH image in the superimposed image is successively updated in accordance with the radiography.

In that case, the radiography control unit 62 intermittently interrupts the initiated partial fluoroscopy at a predetermined time interval (every few seconds), and performs the radiography during the interruption. Alternatively, the radiography control unit 62 interrupts the initiated partial fluoroscopy after the change of the relative positions of the object S and the X-ray detection device 27 (a first example of the partial fluoroscopy described later), and performs the radiography during the interruption. When the interruption of the partial fluoroscopy is initiated, the radiography control unit 62 switches the aperture blades B1-B4 to the positioning for radiography (full-open: as illustrated in FIG. 3A) from the positioning for fluoroscopy. When the interruption of the partial fluoroscopy (radiography) is terminated, the aperture blades B1-B4 are switched from the positioning for radiography to the positioning for fluoroscopy, and the partial fluoroscopy is restarted.

The partial fluoroscopy control unit 63 has an irradiation field limiting unit 631, a partial fluoroscopy initiating unit 632, an irradiation field change determination unit 633, an irradiation field changing unit 634, and a partial fluoroscopy terminating unit 635.

The irradiation field limiting unit 631 has a function to drive the aperture blades of the movable aperture device 262 of the X-ray irradiation device 26 via the controller 4 to narrow (contract) the X-ray irradiation field in accordance with the instruction input from the input device 57. As shown in FIGS. 3A and 3B, the irradiation field limiting unit 631 has a function to contract the X-ray irradiation field from the radiography irradiation field Fs to the partial fluoroscopy irradiation field Ff by contracting an irradiation domain of X-ray from the radiography opening Os to the partial fluoroscopy opening Of.

The partial fluoroscopy initiating unit 632 has a function to initiate operation of the high-voltage supply device 28 and the X-ray detection device 27 via the controller 4 and initiate the partial fluoroscopy with the X-ray irradiation field narrowed by the irradiation field limiting unit 631 in accordance with the instruction input from the input device 57. Further, the partial fluoroscopy initiating unit 632 has a function to initiate the generation of the partial fluoroscopy image as a dynamic image by controlling the X-ray image generator 52, the X-ray image processor 53, and the display processor 55, and initiate displaying, on the display device 56, the image in which the partial fluoroscopy image is superimposed on a part of the LIH image generated by the radiography control unit 62.

The irradiation field change determination unit 633 determines, during the partial fluoroscopy, whether to change (slide, enlarge/contract) the X-ray irradiation field set by the irradiation field limiting unit 631, and whether to further change the X-ray irradiation field changed by the irradiation field changing unit 634. The method for determination by the irradiation field change determination unit 633 will be stated below.

The irradiation field changing unit 634 has a function to drive the aperture blades of the movable aperture device 262 of the X-ray irradiation device 26 via the controller 4 to change the X-ray irradiation field set by the irradiation field limiting unit 631 in a case where it is determined that the X-ray irradiation field is to be changed during the partial fluoroscopy by the irradiation field change determination unit 633. The irradiation field changing unit 634 changes, during the partial fluoroscopy, the partial fluoroscopy irradiation field Ff shown in FIG. 3B, and further changes the partial fluoroscopy irradiation field Ff after the change.

Figure 6A:
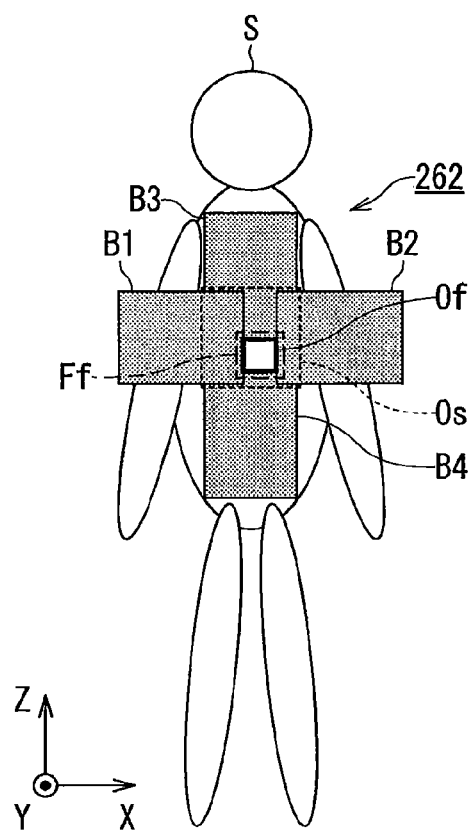
FIGS. 6A and 6B are diagrams for explaining a slide as a change of the X-ray irradiation field.
Figure 6B:
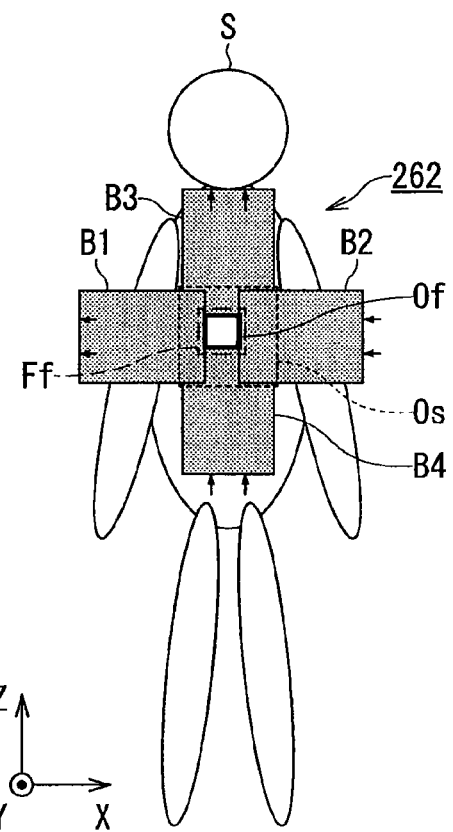

FIGS. 6A and 6B are diagrams for explaining a slide as the change of the X-ray irradiation field. FIGS. 6A and 6B are diagrams in which the movable aperture device 262 is seen from the side of the X-ray tube 261.

The movable aperture device 262 shown in FIG. 6A is same as that in FIG. 3B, and shows the positioning of the aperture blades B1-B4 in the X-ray irradiation field during the partial fluoroscopy before a slide. The movable aperture device 262 shown in FIG. 6B shows the positioning of the aperture blades B1-B4 in the X-ray irradiation field during the partial fluoroscopy after the slide.

From the state shown in FIG. 6A, the positions in the X-axis direction of the aperture blades B1 and B2 movable in the X-axis direction are adjusted, and the positions in the Z-axis direction of the aperture blades B3 and B4 movable in the Z-axis direction are adjusted, so that the partial fluoroscopy opening Of is slid within the radiography opening Os (shown in FIG. 6B). In other words, in accordance with sliding of the partial fluoroscopy opening Of in the radiography opening Os, the X-ray irradiation field is slid.

Figure 8:
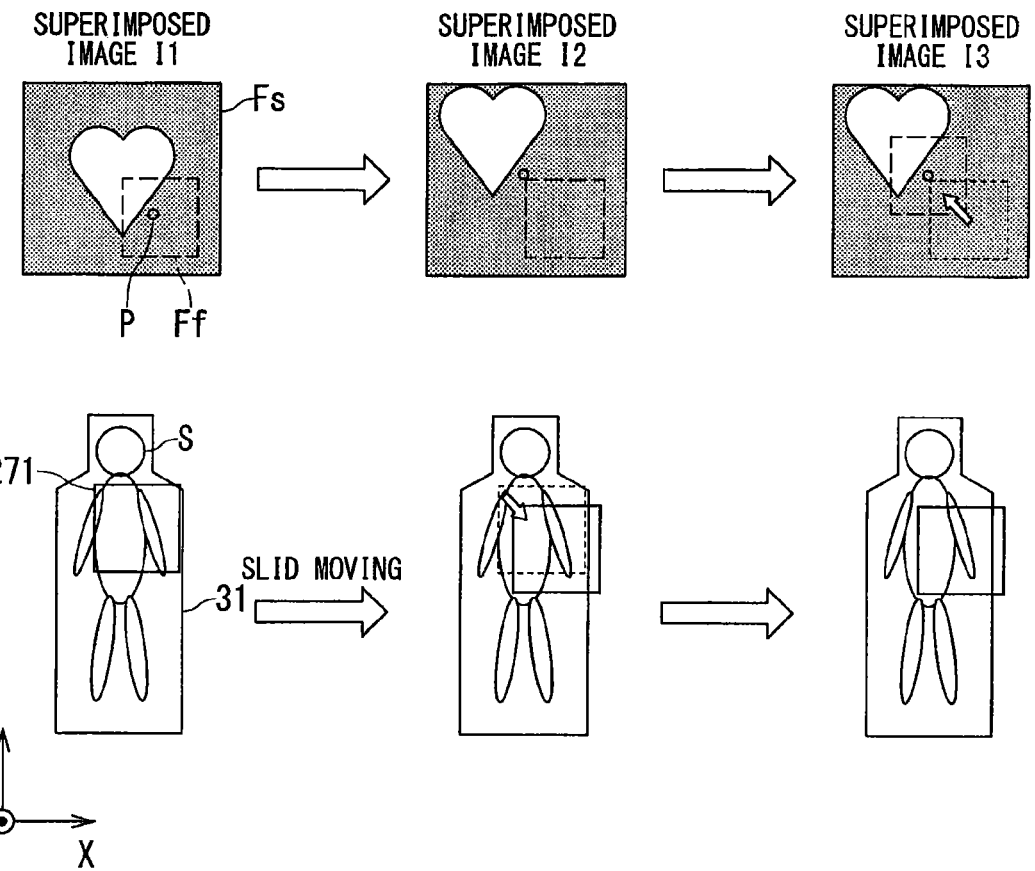
FIG. 8 is a diagram for explaining a first example of partial fluoroscopy by the X-ray diagnosis apparatus according to the present embodiment.
Figure 9:
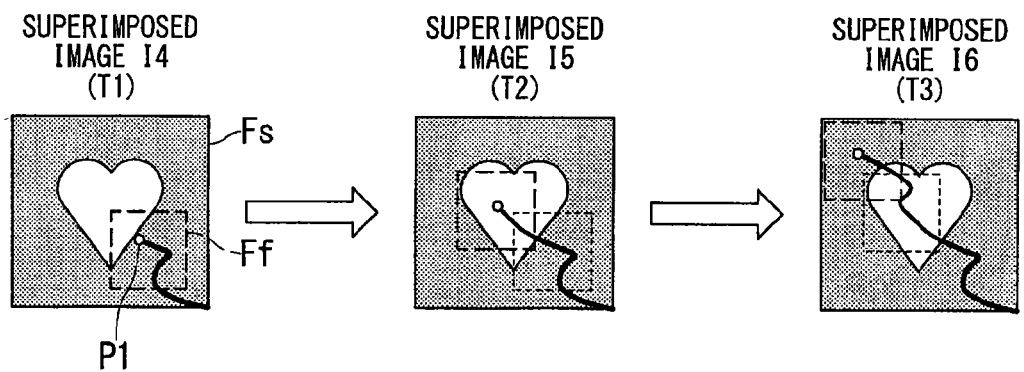
FIG. 9 is a diagram for explaining a second example of partial fluoroscopy by the X-ray diagnosis apparatus according to the present embodiment.

Sliding of the X-ray irradiation field during the partial fluoroscopy described in FIGS. 6A and 6B may be performed in accordance with the description using FIGS. 8 and 9, or may be performed in accordance with the instruction input from the input device 57.

Figure 7A:
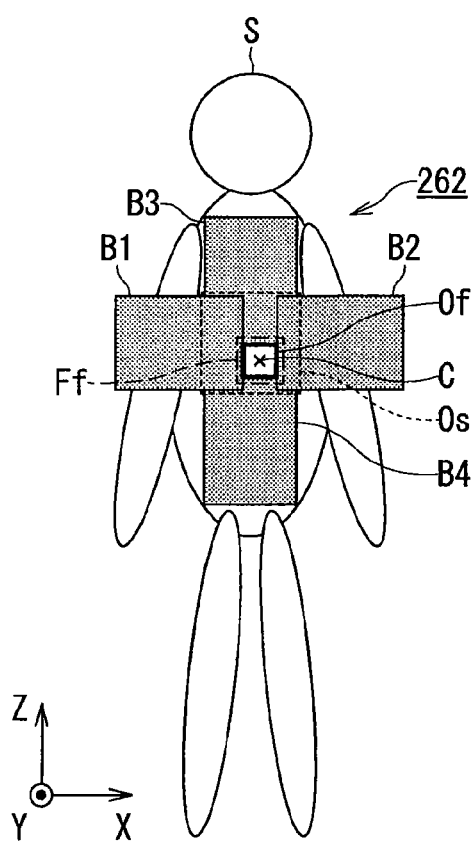
FIGS. 7A and 7B are diagrams for explaining enlargement as the change of the X-ray irradiation field.
Figure 7B:
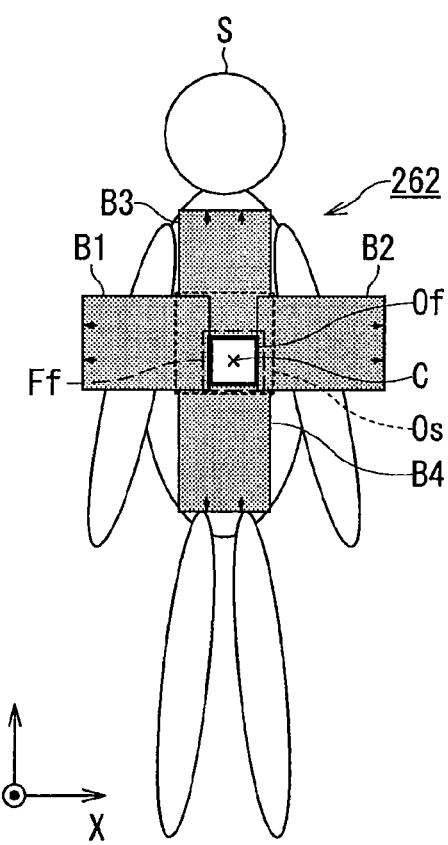

FIGS. 7A and 7B are diagrams for explaining enlargement as the change of the X-ray irradiation field. FIGS. 7A and 7B are diagrams in which the movable aperture device 262 is seen from the side of the X-ray tube 261.

The movable aperture device 262 shown in FIG. 7A is same as that in FIG. 3B, and shows the positioning of the aperture blades B1-B4 of the X-ray irradiation field during the partial fluoroscopy before enlargement, and the movable aperture device 262 shown in FIG. 7B shows the positioning of the aperture blades B1-B4 of the X-ray irradiation field during the partial fluoroscopy after the enlargement.

In accordance with the instruction input from the input device 57, the positions in the X-axis direction of the aperture blades B1 and B2 movable in the X-axis direction are adjusted, and the positions in the Z-axis direction of the aperture blades B3 and B4 movable in the Z-axis direction are adjusted from the state shown in FIG. 7A. Thereby, the partial fluoroscopy opening Of is enlarged within the radiography opening Os with an X-ray irradiation field center C as the center (shown in FIG. 7B). The positions of the aperture blades B1-B4 are changed by the same amount. In other words, in accordance with the enlargement of the partial fluoroscopy opening Of within the radiography opening Os, the X-ray irradiation field is enlarged with the X-ray irradiation field center C as the center.

Referring back to FIG. 5, the partial fluoroscopy terminating unit 635 has a function to terminate the operation of the high-voltage supply device 28 and the X-ray detection device 27 in accordance with the instruction input from the input device 57 via the controller 4 and terminates the partial fluoroscopy.

Next, differences between the partial fluoroscopy of the conventional techniques and the partial fluoroscopy of the X-ray diagnosis apparatus 1 according to the present embodiment will be described.

(First Example of Partial Fluoroscopy)

FIG. 8 is a diagram for explaining a first example of the partial fluoroscopy by the X-ray diagnosis apparatus 1 according to the present embodiment.

FIG. 8 shows three superimposed images I1-I3 (upper row) and relative positions of the object S and the X-ray detection device 27 (FPD 271) at the time when the LIH images included in the respective superimposed images I1-I3 (lower row) are generated. Each of the superimposed images I1-I3 includes a portion of interest P of the object S.

With the superimposed image I1 being displayed during the partial fluoroscopy, the relative positions of the object S and the X-ray detection device 27 are changed. For example, in a case where the X-ray detection device 27 is slid in the horizontal direction via the sliding mechanism 21 during the partial fluoroscopy, or, where the table-top 31 is slid in the horizontal direction via the bed system 3, the superimposed image I2 will be displayed. Here, the superimposed image I2 (the same of the superimposed image I3) is based on the LIH image obtained by the radiography after the change of the relative positions of the object S and the X-ray detection device 27. This is because when the relative positions of the object S and the X-ray detection device 27 are changed, a relative positional relationship between the LIH image that is a static image before the change of the relative positions of the object S and the X-ray detection device 27 and the partial fluoroscopy image that is a dynamic image after the change of the relative positions of the object S and the X-ray detection device 27 is offset from one another.

Then, in a case where, during the partial fluoroscopy, a slide in the horizontal direction of the X-ray detection device 27 is detected, or a slide in the horizontal direction of the table-top 31 is detected, the irradiation field change determination unit 633 determines to change the partial fluoroscopy irradiation field. The irradiation field changing unit 634 drives the aperture blades B1-B4 so as to slide the partial fluoroscopy irradiation field Ff within the radiography irradiation field Fs in accordance with the amount of slide of the X-ray detection device 27 as explained by using FIG. 6A and FIG. 6B. Therefore, the partial fluoroscopy irradiation field Ff is slid so that the fluoroscopy position of the object S does not change within the radiography irradiation field Fs. After the slide of the partial fluoroscopy irradiation field Ff, the superimposed image I3 in which the partial fluoroscopy image is superimposed on a part of the LIH image is generated and displayed.

The case where the relative positions of the object S and the X-ray detection device 27 are changed with the superimposed image I1 being displayed during the partial fluoroscopy, is not limited to the case where the X-ray detection device 27 is slid in the horizontal direction and the case where the table-top 31 is slid in the horizontal direction. Also in the case of rotational motion of the vertical axis rotation mechanism 22, the C-arm rotating mechanism 24, and the C-arm 25 of the imaging system 2, and an arc motion of the C-arm 25, the irradiation field changing unit 634 drives the aperture blades of the movable aperture device 262 so as to slide the partial fluoroscopy irradiation field Ff within the radiography irradiation field Fs in accordance with the amount of rotation and the amount of arc motion.

A table may be provided in advance for the relationship between the amounts of the rotational motion and the arc motion and the amount of the slide of the partial fluoroscopy irradiation field Ff.

The amount of the slide of the sliding mechanism 21 of the imaging system 2 and the bed system 3, the amount of the rotational motion of the vertical axis rotation mechanism 22, the C-arm rotating mechanism 24, and the C-arm 25 of the imaging system 2, and the amount of the arc motion of the C-arm 25 are each measurable by a position sensors (not shown).

(Second Example of Partial Fluoroscopy)

FIG. 9 is a diagram for explaining a second example of the partial fluoroscopy according to the X-ray diagnosis apparatus 1 according to the present embodiment.

FIG. 9 shows two superimposed images I4-I6. Each of the superimposed images I4-I6 includes a catheter tip end P1 as the portion of interest P of the object S.

The catheter tip end P1 detected on the partial fluoroscopy image of the superimposed image I4 displayed at a time T1 during the partial fluoroscopy moves at a time T2 to a position that is different from the position at the time T1. In a case where the movement of the catheter tip end P1 on the partial fluoroscopy image is detected during the partial fluoroscopy, the irradiation field change determination unit 633 determines to change the partial fluoroscopy irradiation field. The irradiation field changing unit 634 drives the aperture blades B1-B4 so as to slide the partial fluoroscopy irradiation field Ff within the radiography irradiation field Fs, in accordance with the amount of movement of the catheter tip end P1 on the partial fluoroscopy image (tracking the movement), as explained by using FIGS. 6A and 6B. Therefore, the partial fluoroscopy irradiation field Ff is slid so that the catheter tip end P1 can be recognized on the partial fluoroscopy image within the radiography irradiation field Fs. After the slide of the partial fluoroscopy irradiation field Ff, the superimposed image I5 in which the partial fluoroscopy image is superimposed on a part of the LIH image is generated and displayed.

Next, the catheter tip end P1 detected on the partial fluoroscopy image of the superimposed image I5 displayed at the time T2, moves at a time T3 to a position that is different from the position at the time T2. In a case where further movement of the catheter tip end P1 on the partial fluoroscopy image is detected during the partial fluoroscopy, the irradiation field change determination unit 633 determines to further change the partial fluoroscopy irradiation field. The irradiation field changing unit 634 drives the aperture blades B1-B4 so as to slide the partial fluoroscopy irradiation field Ff within the radiography irradiation field Fs, in accordance with the amount of movement of the catheter tip end P1 detected on the partial fluoroscopy image, as explained by using FIGS. 6A and 6B. Therefore, the partial fluoroscopy irradiation field Ff is slid so that the catheter tip end P1 can be recognized on the partial fluoroscopy image within the radiography irradiation field Fs. After the slide of the partial fluoroscopy irradiation field Ff, the superimposed image I6 in which the partial fluoroscopy image is superimposed on a part of the LIH image is generated and displayed.

(Third Example of Partial Fluoroscopy)

Figure 10:
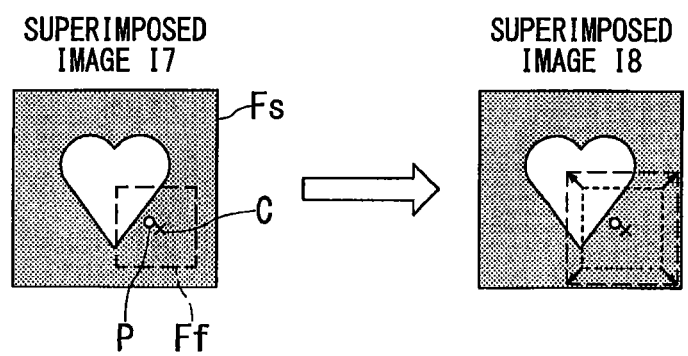
FIG. 10 is a diagram for explaining a third example of partial fluoroscopy by the X-ray diagnosis apparatus according to the present embodiment.

FIG. 10 is a diagram for explaining a third example of the partial fluoroscopy according to the X-ray diagnosis apparatus 1 according to the present embodiment.

FIG. 10 shows two superimposed images I7 and I8. Each of the superimposed images I7 and I8 includes the portion of interest P of the object S.

With the superimposed image I7 being displayed during the partial fluoroscopy, the instruction of enlargement/contraction of the partial fluoroscopy irradiation field is input from the input device 57. In a case where the enlargement/contraction of the partial fluoroscopy irradiation field is instructed from the input device 57 during the partial fluoroscopy, the irradiation field change determination unit 633 determines to change the partial fluoroscopy irradiation field. For example, in a case where the enlargement of the partial fluoroscopy irradiation field is instructed from the input device 57, the irradiation field changing unit 634 drives the aperture blades B1-B4 so that the partial fluoroscopy irradiation field Ff is enlarged within the radiography irradiation field Fs with the X-ray irradiation field center C as the center, as explained by using FIGS. 7A and 7B, in accordance with the instruction input from the input device 57. Therefore, the partial fluoroscopy irradiation field Ff is enlarged with the X-ray irradiation field center C as the center within the radiography irradiation field Fs. After the enlargement of the partial fluoroscopy irradiation field Ff, a superimposed image I8 in which the partial fluoroscopy image is superimposed on a part of the LTH image is generated and displayed.

(Fourth Example of Partial Fluoroscopy)

Figure 11:
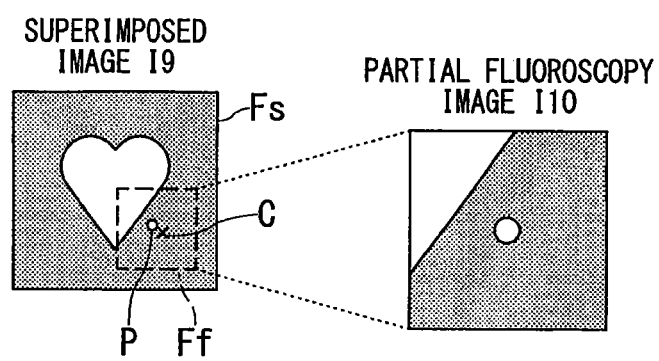
FIG. 11 is a diagram for explaining a fourth example of partial fluoroscopy by the X-ray diagnosis apparatus according to the present embodiment.
Figure 12:
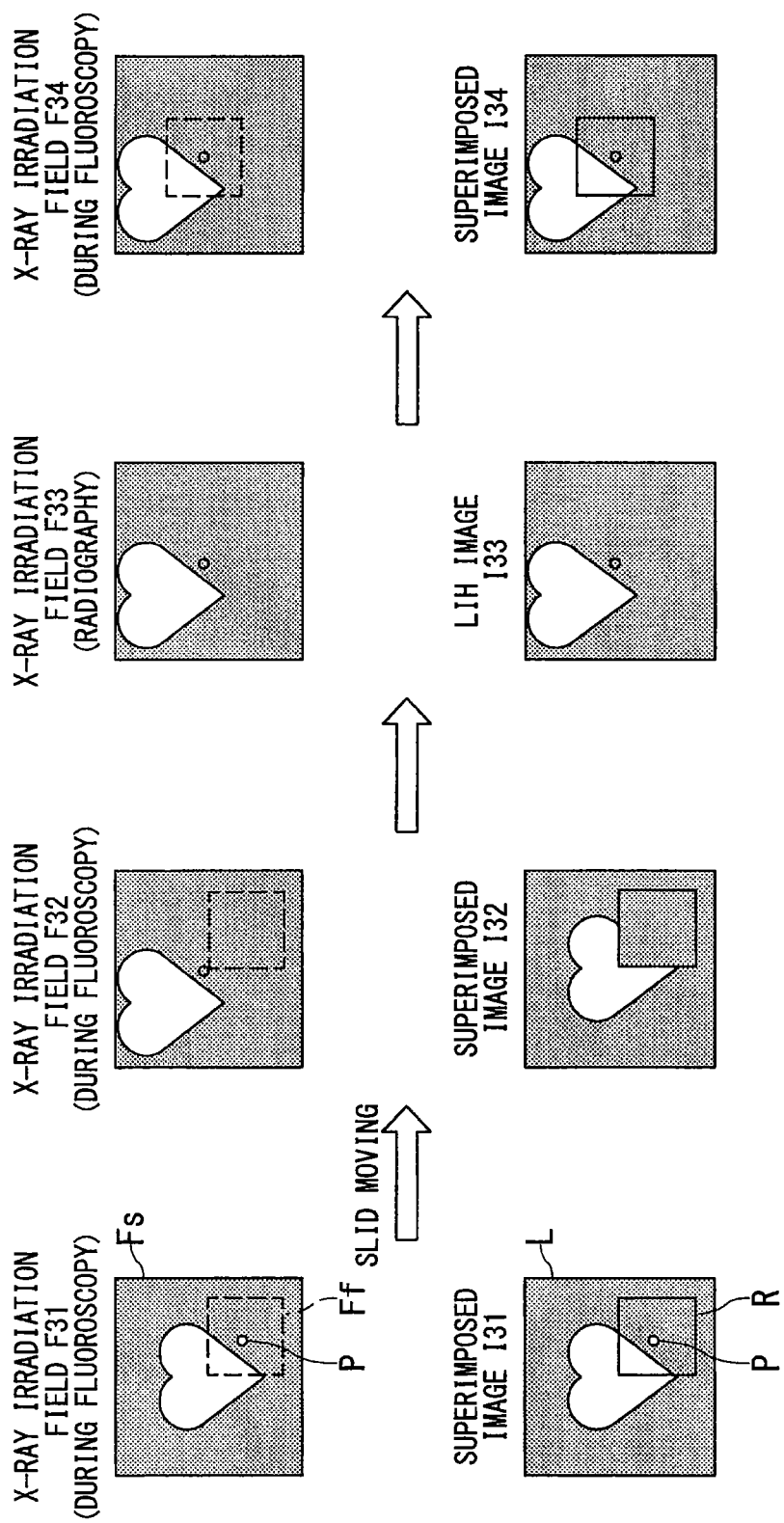
FIG. 12 is a diagram for explaining a first example of partial fluoroscopy of conventional techniques.
Figure 13:
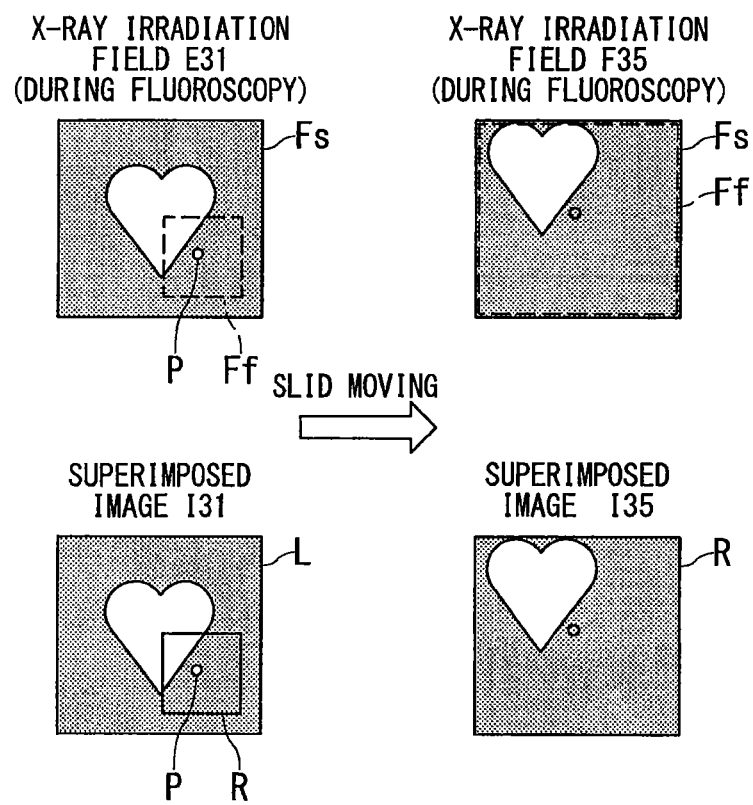
FIG. 13 is a diagram for explaining a second example of partial fluoroscopy of conventional techniques.

FIG. 11 is a diagram for explaining a fourth example of the partial fluoroscopy of the X-ray diagnosis apparatus 1 according to the present embodiment.

FIG. 11 shows two images I9 and I10. Each of the images 19 and 110 includes the portion of interest P of the object S.

With the superimposed image I9 being displayed during the partial fluoroscopy, an instruction of zoom-in/zoom-out of the partial fluoroscopy irradiation field is input from the input device 57. In a case where the zoom-in of the partial fluoroscopy irradiation field is instructed from the input device 57 during the partial fluoroscopy, the irradiation field change determination unit 633 determines to change the partial fluoroscopy irradiation field. For example, in a case where the zoom-in of the partial fluoroscopy irradiation field is instructed from the input device 57, the irradiation field changing unit 634 performs the zoom-in on the partial fluoroscopy image as a part of the superimposed image I9 with the X-ray irradiation field center C as the center, in accordance with the instruction input from the input device 57. The partial fluoroscopy image I10 zoomed-in is generated and displayed. Therefore, when the partial fluoroscopy image is zoomed-in/zoomed-out after the change of the partial irradiation field Ft explained in FIGS. 8 and 9, the portion of interest P does not deviate from the partial fluoroscopy irradiation field Ff.

According to the X-ray diagnosis apparatus 1 and the control method thereof of the present embodiment, the partial fluoroscopy irradiation field Ff can be changed in real-time during the partial fluoroscopy. In particular, according to the X-ray diagnosis apparatus 1 of the present embodiment, efficiency of exams and therapies can be improved where, during the partial fluoroscopy, the imaging system 2 or the bed system 3 is driven to change the relative positions of the object S and the X-ray detection device 27 (FPD 271), or where the catheter tip end P1 is tracked on the image. Further, it becomes possible to change any partial fluoroscopy irradiation field, or perform aperture operations during the partial fluoroscopy, resulting in a significant reduction of operation stress for the operator, in addition to exposure reduction effect that the partial fluoroscopy originally provides, to enhance usability.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising:
   an X-ray irradiation device configured to irradiate an object with an X-ray, the device including an X-ray source configured to generate an X-ray and a movable aperture device including multiple aperture blades configured to form an X-ray irradiation field;
   an X-ray detection device disposed to be opposed to the X-ray irradiation device and configured to detect the X-ray;
   a retainer configured to retain the X-ray irradiation device and the X-ray detection device; and
   processing circuitry configured to
      generate a last image hold (LIH) image as a static image by using a radiography irradiation field as the X-ray irradiation field,
      generate fluoroscopy images by using a fluoroscopy irradiation field as the X-ray irradiation field, the fluoroscopy irradiation field being narrower than the radiography irradiation field,
      generate superimposed images in which the fluoroscopy images are superimposed on a part of the LIH image,
      display the superimposed images on a display device,
      slides the aperture blades to enlarge or contact the fluoroscopy irradiation field of the fluoroscopy images, included in the corresponding superimposed images, with a fixed center of the fluoroscopy irradiation field, when an enlarging or contracting instruction of the fluoroscopy irradiation field is input, while the superimposed images are displayed, from an input device, and
      enlarge or contact the fluoroscopy irradiation field of the fluoroscopy images, included in the corresponding superimposed images, with the fixed center, when the enlarging or contacting instruction of the fluoroscopy irradiation field is input, while the superimposed images are displayed, from the input device,
   wherein an area which is inside a first fluoroscopy image before the contracting and which is outside a second fluoroscopy image after the contracting is applied, indicates a part of the LIH image.

2. The X-ray diagnosis apparatus according to claim 1, wherein the processing circuitry is configured to control, when relative positions of the object and the X-ray detection device are changed with the displayed superimposed image, the moveable aperture device so as to slide the aperture blades to enlarge or contact the fluoroscopy irradiation field within the radiography irradiation field without changing a fluoroscopy position to generate the fluoroscopy images for the object.

3. The X-ray diagnosis apparatus according to claim 2, wherein the irradiation field changing unit slides the aperture blades to enlarge or contact the fluoroscopy irradiation field in accordance with an amount that at least one of the X-ray detection device and the retainer slides.

4. The X-ray diagnosis apparatus according to claim 2, wherein the processing circuitry is configured to control the moveable aperture device so as to slide the aperture blades to enlarge or contact the fluoroscopy irradiation field in accordance with an amount of rotational motion and an amount of arc motion of the retainer.

5. The X-ray diagnosis apparatus according to claim 1, wherein the processing circuitry controls, while the superimposed image is displayed, the movable aperture device so as to slide the aperture blades to enlarge or contact the fluoroscopy irradiation field within the radiography irradiation field in accordance with an amount of movement of a catheter tip end detected on the fluoroscopy image in such a manner that the catheter tip end is always recognized on the fluoroscopy image.

6. The X-ray diagnosis apparatus according to claim 1, wherein the processing circuitry updates the radiography image superimposed on the superimposed image by temporarily interrupting generation of the fluoroscopy image after initiation of the generation of the fluoroscopy image, and generating the radiography image during the interruption.

7. The X-ray diagnosis apparatus according to claim 6, wherein the processing circuitry intermittently interrupts the generation of the fluoroscopy image at a predetermined time interval, and generates the radiography image during the interruption.

8. The X-ray diagnosis apparatus according to claim 6, wherein the processing interrupts the generation of the fluoroscopy image after relative positions of the object and the X-ray detection device are changed, and generates the radiography image during the interruption.

9. A control method for an X-ray diagnosis apparatus including an X-ray irradiation device configured to irradiate an object with an X-ray, the device including an X-ray source configured to generate an X-ray and a movable aperture device including multiple aperture blades configured to form an X-ray irradiation field; an X-ray detection device disposed to be opposed to the X-ray irradiation device and configured to detect the X-ray; a retainer configured to retain the X-ray irradiation device and the X-ray detection device; the method comprising:
generating a last image hold (LIH) image as a static image by using a radiography irradiation field as the X-ray irradiation field;
generating fluoroscopy images by using a fluoroscopy irradiation field as the X-ray irradiation field, the fluoroscopy irradiation field being narrower than the radiography irradiation field;
generating superimposed images in which the fluoroscopy images are superimposed on a part of the last image hold (LIH) image;
displaying the superimposed images on a display device; and
sliding the aperture blades to enlarge or contact the fluoroscopy irradiation field of the fluoroscopy images, included in the corresponding superimposed images, with a fixed center of the fluoroscopy irradiation field, when an enlarging or contacting instruction of the fluoroscopy irradiation field is input, while the superimposed images are displayed, from an input device, and
enlarging or contacting the fluoroscopy irradiation field of the fluoroscopy images, included in the corresponding superimposed images, with the fixed center, when the enlarging or contacting instruction of the fluoroscopy irradiation field is input, while the superimposed images are displayed, from the input device,
wherein an area which is inside a first fluoroscopy image before the contracting and which is outside a second including the second fluoroscopy image is displayed, a part of the LIH image.

10. The control method according to claim 9, further comprising:
when relative positions of the object and the X-ray detection device are changed within the displayed superimposed images, controlling the movable aperture device so as to slide the aperture blades to enlarge or contact the fluoroscopy irradiation field within the radiography irradiation field without changing a fluoroscopy position to generate the fluoroscopy images for the object.

11. The control method according to claim 10, further comprising:
sliding the aperture blades to enlarge or contact the fluoroscopy irradiation field in accordance with an amounts that at least one of the X-ray detection device and the retainer slides.

12. The control method according to claim 10, further comprising:
controlling the movable aperture device so as to slide the aperture blades to enlarge or contact the fluoroscopy irradiation field in accordance with an amount of rotational motion and an amount of arc motion of the retainer.

13. The control method according to claim 9, further comprising:
controlling the movable aperture device so as to slide the aperture blades to enlarge or contact the fluoroscopy irradiation field within the radiography irradiation field in accordance with an amount of movement of a catheter tip end detected on the fluoroscopy image in such a manner that the catheter tip end is always recognized on the fluoroscopy image.

14. The control method according to claim 9, wherein the step of generating the LIH image updating the LIH image superimposed on the superimposed image by temporarily interrupting generation of the fluoroscopy image after initiation of the generation of the fluoroscopy image, and generating the radiography image during the interruption.

15. The control method according to claim 14, wherein the step of generating the LIH image intermittently interrupting the generation of the fluoroscopy image at a predetermined time interval, and generating the LIH image during the interruption.

16. The control method according to claim 14, wherein the step of generating the LIH image comprises interrupting the generation of the fluoroscopy image after relative positions of the object and the X-ray detection device are changed, and generates the LIH image during the interruption.

\* \* \* \* \*